United States Patent [19]

Frei

[11] Patent Number: 5,507,825
[45] Date of Patent: Apr. 16, 1996

[54] KIT FOR AN ARTIFICIAL JOINT SOCKET, IN PARTICULAR A HIPJOINT SOCKET

[75] Inventor: Heribert Frei, Schaffhausen, Switzerland

[73] Assignee: Sulzer Medizinaltechnik AG, Winterthur, Switzerland

[21] Appl. No.: 200,132

[22] Filed: Feb. 22, 1994

[30] Foreign Application Priority Data

Apr. 15, 1993 [EP] European Pat. Off. .............. 93810273

[51] Int. Cl.⁶ .................... A61F 2/32; A61F 2/34
[52] U.S. Cl. .................... 623/22; 623/11; 623/16; 623/18
[58] Field of Search .......................... 623/11, 16, 18–19, 623/22–23; 606/60, 65–66, 69–73

[56] References Cited

U.S. PATENT DOCUMENTS

| | | | |
|---|---|---|---|
| 4,840,632 | 6/1989 | Kampner | 623/22 |
| 4,990,161 | 2/1991 | Kampner | 623/23 |
| 5,021,062 | 6/1991 | Adrey et al. | 623/16 |
| 5,314,487 | 5/1994 | Schryver et al. | 623/22 |
| 5,334,184 | 8/1994 | Bimman | 623/16 |
| 5,360,452 | 11/1994 | Engelhardt et al. | 606/71 |

FOREIGN PATENT DOCUMENTS

| | | | |
|---|---|---|---|
| 0085493 | 8/1983 | European Pat. Off. | 606/66 |
| 2666983 | 3/1992 | France | 623/23 |

Primary Examiner—Randall L. Green
Assistant Examiner—P. Zuttarelli
Attorney, Agent, or Firm—Townsend and Townsend and Crew

[57] ABSTRACT

A kit for implanting a socket joint implant has an outer cup (1), an inner cup (2) and fasteners (3, 3a) which are fitted to radially project from the outer cup (1). Each fastener includes a bearer plate (17) arranged on a shaft-like supporting part (18) which is able to bear in an anchoring bore (6) in the bone tissue (5), and a head part (20) which is connected detachably to the supporting part (18) and can be screwed tight from the inside of the outer cup (1) into a guide bore (11) of the cup. The supporting part (18) has a diameter (A) which is less than the diameter (d1) of the guide bore (11). The kit is pre-assembled outside the region of implantation and positioned in the region of implantation while the fasteners (3, 3a) are pulled in towards the center of the outer cup (1). The fasteners (3, 3a) are then pushed into the anchoring bores (6) and screwed tight to the outer cup (1) with head parts (20). The kit is adaptable to different anatomical conditions and may be employed as a replacement for a part of the pelvis missing in the region of the hip socket.

7 Claims, 1 Drawing Sheet

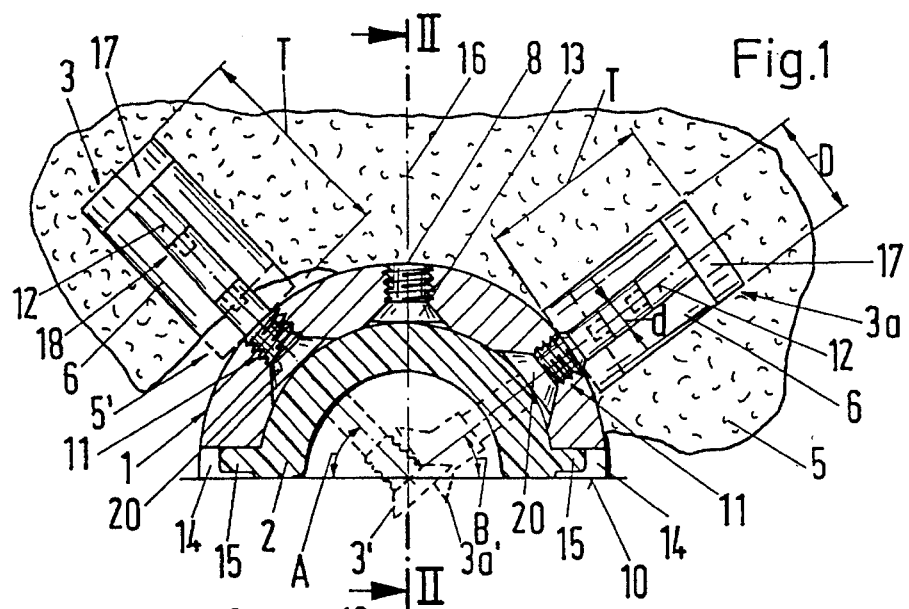
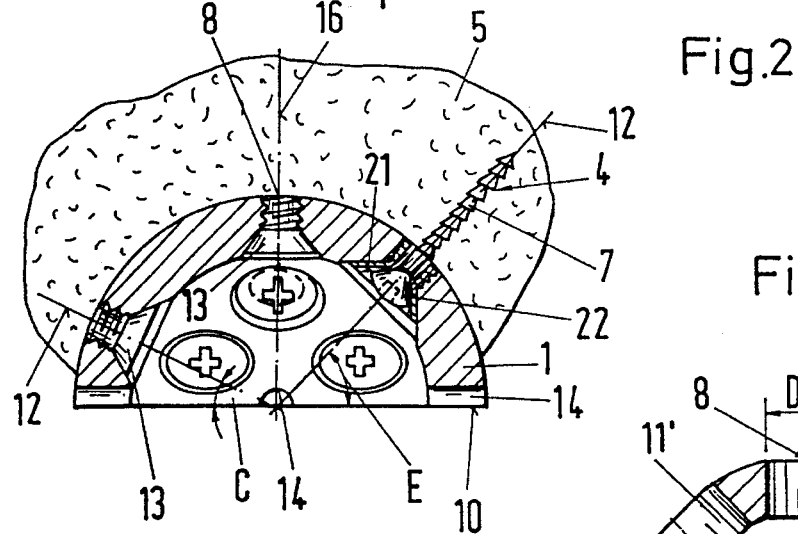
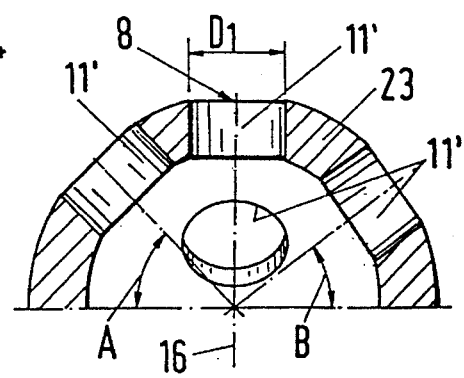
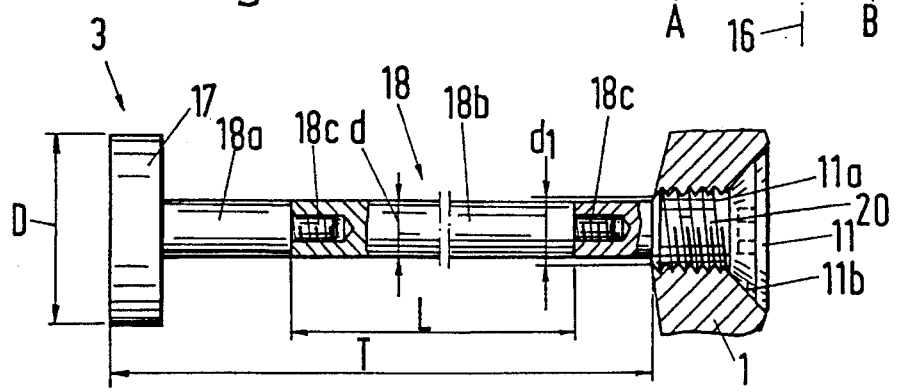

KIT FOR AN ARTIFICIAL JOINT SOCKET, IN PARTICULAR A HIPJOINT SOCKET

The invention is concerned with a kit for building an artificial joint socket, in particular a hipjoint socket with a metallic outer cup with guide bores of different angularity, each provided with a thread, an inner cup which may be inserted in the outer cup, and at least one fastener which is fastened to the outer cup for introduction into an anchoring bore formed in the bone tissue. The fastener has a head part which is introduced from inside the outer cup into one of the guide bores.

The invention is further concerned with a method of fastening a joint socket of that kind into the bone tissue.

Such a kit, known from U.S. Pat. No. 5,021,062, comprises a bone screw which is screwed into the bone tissue or a bone nail as a fastener which is introduced from inside through the guide bore into the bone tissue and is screwed into the outer cup by a threaded portion formed on the head part. The bone screw has a second portion of thread which may be screwed into the thread in the bone. Its outer diameter and pitch are greater than the outer diameter and pitch of the first portion of thread which may be screwed into the guide bore in the outer cup. The core diameter and the shape of thread of the second portion of thread are so chosen that two successive turns of this second portion of thread may be carried over two successive turns of thread in the guide bore without engaging in them.

The guide bores in the outer cup can correspondingly each be executed with at most only two turns of thread effective for screwing the fastener, in order to enable unimpeded screwing of the bone screw into the bone tissue. Hence in the known arrangement only these relatively short portions of thread are available for the transmission of the supporting forces, which occur at any time and under certain circumstances can be considerable, and for ensuring a correspondingly highly loaded screw connection between the bone screw and the outer cup. Thus, the known kit has only use for applications in which the anatomical conditions in the region of implantation may vary over relatively wide limits, e.g., as a substitute for part of the pelvis which is missing in the region of the hipjoint, since in many such cases a secure fastening of the joint socket by bone screws is not possible, so that an assortment of a number of bone screws of different lengths must be kept in stock to assure the availability of kits for even relatively rare applications of that kind.

SUMMARY OF THE INVENTION

It is an object of the invention to create an improved kit of the above-mentioned kind. Its construction guarantees a loading of the bone tissue and the cooperating parts which is more favorable compared to what was attainable in the past and allows the use of components which are simple to produce, readily adjustable and may be adapted with little expenditure of labor to different anatomical conditions and positioned with respect to the region of implantation.

A kit made in accordance with the invention allows a dimensioning of the bearer plate of the fastener which is independent of the diameters of the guide bores made in the outer cup. Without weakening the outer cup the bearer plate can be given a relatively large effective bearing area and thereby enables the transmission of the supporting forces with minimum loading of the bone tissue by pressure. The present invention further allows a simple change of the length of the fastener to adapt it to different anatomical conditions, e.g., to bridge over a part of the bone tissue which is missing or is to be replaced, so that even in such cases an exact positioning of the joint socket is attained.

A further advantage of the kit made in accordance with the invention is that the outer cup is assembled beforehand prior to its implantation and remote from the implant site with the fastener or fasteners which have the required support length. The assembled cup is then positioned at the region of implantation, the fasteners are pulled in towards the center of the outer cup, and bearer plates on the outside of the outer cup are aligned with the anchoring bores in the bone tissue. The fastener is then introduced in a radial direction into the anchoring bore by a simple shifting or advancing movement and positioned with the outer cup by screwing the head part. In that case the guide bores in the outer cup and the head part may each include threads which cooperate over a relatively long common portion and to guarantee a robust connection, resistant against bending, between the outer cup and the fastener.

The method of the present invention enables, with little expenditure of time and labor, an optimum preparation of the region of implantation intended for receiving the joint socket and a simple insertion of the kit which may be assembled during the operation to correspond with the anatomical conditions and introduced as a compact unit into the region of implantation.

BRIEF DESCRIPTION OF THE DRAWINGS

FIG. 1 shows, in section, parts of a kit made in accordance with the invention;

FIG. 2 shows further parts of the kit and is a section taken on line II—II in FIG. 1;

FIG. 3 shows a further part of the kit, in section, which is used as a tool or jig for preparing a region of implantation; and FIG. 4 is an enlarged detail, partially in section, of a portion of the kit shown in FIG. 1.

DETAILED DESCRIPTION OF THE PREFERRED EMBODIMENTS

The kit according to FIGS. 1 and 2 comprises a metallic outer cup 1 in the form of a hollow hemisphere, a likewise hemispherically shaped inner cup 2 which may be inserted in it, and fasteners 3, 3a and 4 which project radially from the outer cup 1 and are fastened into the bone tissue 5 of part of a human pelvis and which position the outer cup 1 outside the bone tissue 5. The illustrated kit is used as a substitute for a part of the pelvis which is missing in the region of the hipjoint. The fasteners 3 and 3a each have the form of a pedestal able to bear in an anchoring bore 6 in the bone tissue. The additional fastener 4 may be a bone nail or, in accordance with FIG. 2, a bone screw 7 which may be screwed into a further anchoring bore in the bone tissue 5.

In the region of its pole 8 the outer cup 1 is provided with a radial guide bore 11 which has an outer threaded portion 11a and an inner portion 11b —conical in the shown embodiment - suitable for receiving a screw head. Further corresponding radial guide bores 11 offset from one another in the circumferential direction between the pole 8 and the equator 10 of the outer cup 1 have inclined axes 12 arranged at different angles A, B, C and D to the plane of the equator 10. The guide bores 11 are each intended for receiving one of the fasteners 3, 3a or 4 or a closure screw 13. Instead of the shown embodiment having two fasteners 3, 3a, it is also possible to provide only one or a number of corresponding fasteners 3, 3a. A number of additional fasteners 4 may equally well be provided. If necessary the additional fastener 4 may also be deleted.

In the region of the equator 10 outer cup 1 may have a number of, e.g., eight recesses 14 distributed about its circumference for receiving lugs 15 on the inner cup 2. The inner cup 2, which may likewise be of metal or, as shown, of plastics, may be snapped into the outer cup 1 with lugs 15 in different angular positions about a polar axis 16 running through the pole 8.

Each fastener 3 or 3a in the form of a pedestal comprises a circular bearer plate 17, a supporting, shaft-like part 18 which in each case can be introduced from outside into one of the guide bores 11, and a head part 20 screwed from the inside of the outer cup 1 into one of the guide bores 11. The bearer plate 17 has a diameter D which is considerably greater than the diameter d of the supporting part 18 which in turn is smaller by a predetermined clearance than the diameter d1 of the threaded portion 11a of the guide bore 11. The latter, in turn, corresponds to the diameter of the core of the threaded portion 20a of the head part 20. The supporting part 18 can be advanced or shifted radially through guide bore 11 and is detachably connected to head part 20 by a threaded pin 18c screwed into a threaded hole in the end face of the head part 20. The head part 20 can be screwed from inside into the guide bore 11.

The supporting part 18 may be made in one piece or it can be assembled from a number of portions, two in accordance with the illustration, 18a and 18b, one portion 18a being firmly connected to the bearer plate 17 and detachably connected to the second portion 18b with a threaded pin 18c. A detachable screw connection to a corresponding threaded pin (not shown) may also be provided between the bearer plate 17 and the supporting part 18 or portion 18a thereof.

As an alternative to the illustrated embodiment, the supporting part 18, or its portion 18b, may extend as far as the threaded portion 20a of the head part 20, in which case the threaded pin 18c extends into a threaded hole in the threaded portion 20a or, as shown, into a continuation of the threaded portion 20a. Corresponding screw connections may also be made to threaded pins 18c projecting from the head part 20 towards the portion 18b, or from the latter towards the portion 18a.

It is useful for the surgeon to keep in stock a number of supporting parts 18, portions 18a or, as in the example shown, of the simple portions 18b of different lengths L in increments of, e.g., millimeters, so that, with relatively low storage costs, portions 18b can readily be selected to correspond to the anatomical conditions present at the time. If necessary they can also be combined with one another. In the embodiment shown in FIG. 1 the fasteners 3 and 3a have different bearer lengths, the fastener 3 exhibiting the greatest bearer length bridging over a region 5' from which the bone tissue 5 is missing, while the shorter fastener 3a projects into the anchoring bore 6 made in an intact region of the bone tissue 5 directly adjoining the outer cup 1.

The bone screw 7—or a corresponding bone nail— may be introduced into the bone tissue 5 through a guide sleeve 21 which may be inserted in the guide bore 11 in question. Closure screws 13 are provided in guide bores 11 which are free of fasteners 3, 3a and 4 to cover them against the bone tissue 5.

In preparation for the implantation of the artificial joint socket an auxiliary device is fastened in the predetermined region of the pelvis. The auxiliary device is part of the kit in the form of a manipulator cup 23 the outer shape of which corresponds to that of the outer cup 1 which is to be inserted in the implantation region in a later step of the method, and is made as a drilling or milling gauge or jig. As shown in FIG. 3 the manipulator cup 23 also has the form of a hollow hemisphere and includes drilled through-holes 11' arranged to correspond to guide bores 11 in the outer cup 1 which is to be implanted. The through-holes 11', intended respectively for the guidance of a drill bit or milling tool, have a diameter D1 which in each case is equal to or greater than the diameter D of the bearer plates 17. The manipulator cup 23 may be made with a considerably greater wall thickness than the outer cup 1, to assure proper and accurate guidance and angularity of the tool. The manipulator cup 23 may be fastened in the region of its pole 8 in known manner, e.g., with a bone screw which, though not shown, may extend, for example, into the bone tissue 5. The manipulator is located in the region of implantation so that it can be turned about the polar axis 16 for positioning it so that two appropriate through-holes 11' are directed towards the portions of the pelvis selected for receiving the fasteners 3 and 3a. A drillbit or milling tool is then introduced into the throughholes 11' for drilling or milling into bone tissue 5 anchoring bores 6, which will receive fasteners 3 and 3a, and pressure bearing end faces for the bearer plates 17. In a like manner a hole intended for receiving the bone screw 7 may be drilled into tissue 5 through one of the through-holes.

After drilling, the depth T of the holes is measured and the manipulator cup 23 may be removed. Thereafter outer cup 1 which is to be inserted later is fitted with fasteners 3 and 3a at the spatial angles A and B of the anchoring bores 6. A supporting part 18 for each is selected from stock —in the illustrated embodiment at least one portion 18b —of appropriate length connected to the bearer plate 17, is introduced into the outer cup 1 from outside through the appropriate guide bore 11, and is connected inside the outer cup 1 to the head part 20 to form the fastener 3 or 3a. Its fitted length corresponds to the measured depth T of the anchoring bore 6 in question. During this phase of the operation closure screws 13 may also be inserted into those guide bores 11 which are free of fasteners 3, 3a and 4.

Before the insertion of the outer cup 1 in the implantation region the fasteners 3 and 3a are each pulled in towards the center of the outer cup 1 into positions 3' or 3a' shown in phantom lines in FIG. 1 so that the associated bearer plate 17 rests against the outside of the outer cup 1. The outer cup 1 prepared in this way can then be handed to the surgeon as an assembled, compact structural unit and is inserted without further manipulation into the bed prepared in the bone. Fasteners 3 and 3a are introduced into the anchoring bores 6 and by screwing the head parts 20 into the outer cup 1 to firmly connect them to the latter. If necessary the bone screw 7 may now be screwed into the corresponding bore in the bone tissue 5.

In a further step the inside of the outer cup 1 may be checked for projecting parts and —after removal of possible deviations from the predetermined inner shape —the inner cup 2 is finally inserted in the outer cup 1.

I claim:

1. A kit for building an artificial joint socket comprising a metallic outer cup having threaded guide bores extending at different angles through the cup, an inner cup for insertion into the outer cup, at least one fastener fastened to the outer cup for introduction into an anchoring bore formed in a bone tissue and terminating in a pressure bearing end face, the fastener including a head part in one of the guide bores and being extendable into the guide bore from inside the outer cup, the fastener, including a bearer plate adapted to be placed into the anchoring bore and bear against the end face of the anchoring bore for the transmission of forces between the bearer plate and the end face of the anchoring bore, the bearer plate having a diameter greater than a diameter of the corresponding guide bore, the fastener further including a shaft-like supporting part attached to the bearer plate and having a diameter less than a diameter of the guide bore, and means detachably connecting the supporting part to the heart part.

2. A kit as in claim 1, including at least one screw connection between the bearer plate and the head part.

3. A kit as in claim 1 wherein the shaft-like supporting part comprises at least two detachably assembled sections.

4. A kit as in claim 3 wherein a supply of at least one of the portions of the supporting part such portions (18a, 18b) is included in the kit, and wherein the portions forming the supply have different lengths.

5. A kit as in claim 1 wherein at least one of the guide bores in the outer cup is free of fasteners and including a closure screw in the at least one guide bore for closing it.

6. A kit as in claim 1 including a manipulator cup having outer dimensions corresponding to outer dimensions of the outer cup for preparing a region of the bone tissue which is to receive the outer cup, the manipulator cup having passages which are arranged to correspond in angularity and orientation to the guide bores in the outer cup, the passages having a diameter which corresponds with the diameter of the bearer plate.

7. A method of fastening an artificial joint socket with a fastener having a bearer plate at one end of the fastener and a head portion, the method comprising the steps of positioning a manipulator cup with respect to a region of bone tissue intended for receiving an outer cup of a socket joint implant, forming an anchoring bore through at least one passage in the manipulator cup and giving the anchoring bore a diameter which corresponds to a diameter of the bearer plate, the anchoring bore terminating in a load bearing end face defined by the bone tissue, measuring a depth of the anchoring bore and removing the manipulator cup from the region of the bone tissue, selecting a fastener as a function of the measured depth, attaching the fastener to the outer cup by extending it through a guide bore in the outer cup which corresponds to the anchoring bore in the bone tissue, drawing the fastener with a head portion thereof towards a center of the outer cup, positioning the outer cup including the attached fastener in the region of the bone tissue, manipulating a portion of the fastener protruding into the inside of the outer cup to align it with the associated anchoring bore in the bone tissue and inserting the bearer plate into the anchoring bore so that it bears against the end face thereof, and threading the head part of the fastener from inside the outer cup into the corresponding guide bore in the outer cup to thereby firmly and rigidly secure the fastener and therewith the bearer plate to the outer cup.

* * * * *